United States Patent [19]

Scheuffgen

[11] Patent Number: 4,777,038

[45] Date of Patent: Oct. 11, 1988

[54] FREE-FLOWING PEARLESCENT CONCENTRATE

[75] Inventor: Ingeborg Scheuffgen, Neuss, Fed. Rep. of Germany

[73] Assignee: Henkel Kommanditgesellschaft auf Aktien, Duesseldorf, Fed. Rep. of Germany

[21] Appl. No.: 864,051

[22] Filed: May 16, 1986

[30] Foreign Application Priority Data

May 28, 1985 [DE] Fed. Rep. of Germany ....... 3519080

[51] Int. Cl.$^4$ ............................ A61K 7/06; A61K 7/08
[52] U.S. Cl. ........................................ 424/70; 514/937
[58] Field of Search ............................................ 424/70

[56] References Cited

U.S. PATENT DOCUMENTS

| | | | |
|---|---|---|---|
| 3,808,329 | 4/1974 | Bolich, Jr. et al. | 424/70 |
| 3,829,563 | 8/1974 | Barry et al. | 424/70 |
| 4,076,800 | 2/1978 | Marsh et al. | 424/70 |
| 4,087,518 | 5/1978 | Smith et al. | 424/70 |
| 4,438,096 | 3/1984 | Preston | 424/70 |
| 4,592,907 | 6/1986 | Akimoto et al. | 424/70 |
| 4,654,163 | 3/1987 | Quack et al. | 424/70 |

FOREIGN PATENT DOCUMENTS

| | | | |
|---|---|---|---|
| 158174 | 10/1985 | European Pat. Off. | 424/70 |
| 56-71021 | 6/1981 | Japan | 424/70 |
| 60-25906 | 2/1985 | Japan | 514/937 |
| 1230413 | 6/1981 | United Kingdom | 424/70 |
| 2121072 | 12/1983 | United Kingdom | 514/937 |

OTHER PUBLICATIONS

International McCutcheon's Emulsifiers & Detergents/Functional Materials, The Manufacturing Confectioner Publishing Co. (1984), pp. 1 and 179.
Cosmetics and Toiletries, 4/1985, vol. 100, p. 62.

*Primary Examiner*—Dale R. Ore
*Attorney, Agent, or Firm*—Ernest G. Szoke; Henry E. Millson, Jr.; Mark A. Greenfield

[57] ABSTRACT

A free-flowing aqueous concentrate for imparting a pearlescent appearance to cosmetics and surfactants and which is compatible with preparations of differing ionicity, containing: a compound of the formula $R^1$-$(OC_nH_{2n})_xOR^2$ wherein $R^1$ is a linear $C_{16-22}$ fatty acyl, $R^2$ is hydrogen or a linear $C_{16-22}$ fatty acyl, n is 2 or 3, and x is 1 to 4; a $C_{12-22}$ fatty acid monoethanolamide; and a nonionic ethylene oxide adduct having an HLB value of 12 to 16; as well as a method for using such concentrate.

29 Claims, No Drawings

FREE-FLOWING PEARLESCENT CONCENTRATE

BACKGROUND OF THE INVENTION

1. Field of the Invention

This invention relates to a pearlescent concentrate in the form of a free-flowing, aqueous dispersion free from ionic surfactants.

2. Statement of the Related Art

Aqueous preparations of surfactants and cosmetic preparations may be given a pearlescent, aesthetically pleasing appearance, by incorporation of substances which, after cooling, precipitate in the form of fine crystals resembling mother-of-pearl in appearance and which remain dispersed in the preparations. Known pearlizers include, for example, the mono- and diesters of ethylene glycol, propylene glycol and oligomeric alkylene glycols of this type or glycerol with $C_{16-22}$ fatty acids and also monoalkanolamides of $C_{12-22}$ fatty acids with $C_2$ or $C_3$ alkanolamines.

It is also known that the pearlizers mentioned form stable dispersions in water or in aqueous surfactant solutions and that the concentrated pearlescent dispersions obtained in this way may be added without heating to the preparations to be pearlized, so that there is no need for the heating and cooling otherwise necessary for incorporation to form the pearlescent crystals.

Pearlescent concentrations based on the pearlizers mentioned above are disclosed, for example, in British Pat. No. 1,230,413 (and corresponding published German patent application No. 16 69 152) as well as in published Japanese patent application No. 56-71,021 (and corresponding Chemical Abstract 95: 156,360). The pearlescent concentrates disclosed in the Japanese reference have the disadvantage that they are not free-flowing and do not form stable, free-flowing dispersions upon dilution with water. This makes the concentrates extremely difficult to handle and process on an industrial scale. The pearlescent concentrates known from British Pat. No. 1,230,413 contain anionic surfactants for stabilizing the dispersion in the liquid state. However, the presence of ionic surfactants is undesirable in numerous applications of pearlescent concentrates of the type in question because imcompatibilities with formulation constituents of opposite ionicity can arise with adverse effects upon the stability of the dispersions.

Accordingly, it is very desirable to provide pearlescent concentrates which are free-flowing at ambient temperatures, (approximately 10° to 30° C.), do not contain any ionic surfactants or dispersants and, nevertheless, remain stable in storage for several months without the pearlescent crystals sedimenting or rising to the surface.

In addition, the pearlescent concentrates should have a pearlescence which is stable to at least 50° C. and which remains intact in the associated preparations despite variations in temperature. The pearlescent crystals should have a high luster and, even after melting or dissolution by heating beyond their melting point, should reassume the same lustrous, uniform crystal form on cooling.

DESCRIPTION OF THE INVENTION

The requirements stated above are satisfied by a pearlescent concentrate in the form of a free-flowing dispersion essentially free from ionic surfactants which comprises:

(A) from 5 to 15% by weight of at least one ester corresponding to the general formula $R^1-(OC_nH_{2n})_x-OR^2$, wherein $R^1$ is a linear $C_{16-22}$ fatty acyl, $R^2$ is hydrogen or a moiety according to $R^1$ which may be the same or different, n is 2 or 3 and x is an integer from 1 to 4;

(B) from 1 to 6% by weight of at least one $C_{12-22}$ fatty acid monoethanolamide;

(C) from 1 to 5% by weight of at least one nonionic ethylene oxide adduct having an HLB value of from 12 to 16; and (D) water in a quantity sufficient (q.s.) to make up 100%, preferably a quantity of about 75 to 90% by weight, all weights being based upon the total weight of the concentrate.

Suitable esters corresponding to the general formula $R^1(OC_nH_{2n})_xOR^2$ are mono- and diesters of ethylene glycol and propylene glycol with higher fatty acids, for example with palmitic acid, stearic acid or behenic acid, or the diesters of diethylene glycol or triethylene glycol with the same fatty acids. Mixtures of mono- and diesters of the glycols mentioned with fatty acid mixtures, for example with hardened tallow fatty acid or with the saturated $C_{16-18}$ fatty acid fraction of tallow fatty acid, are also suitable. The ethylene glycol mono and/or diester or palmitic and/or stearic acid is particularly suitable.

Suitable $C_{12-22}$, preferably $C_{12-18}$ fatty acid monoethanolamides are lauric acid monoethanolamide, myristic acid monoethanolamide, palmitic and/or stearic acid monoethanolamide and, preferably, the monoethanolamide of the $C_{12-18}$ fraction of coconut oil fatty acid.

Suitable and preferred nonionic ethylene oxide adducts are the adducts of 6 to 20 mols of ethylene oxide with fatty alcohols, fatty acids, fatty amides or alkanolamides, the fatty alkyl or fatty acyl moieties present preferably containing from 12 to 22 carbon atoms. Ethylene oxide adducts with alkylphenols, particularly with alkylphenols containing a $C_{8-16}$ alkyl, are also suitable and preferred. Finally, ethylene oxide adducts with fatty acid-polyol partial esters, for example with glycerol monoesters, with pentaerythritol monoesters, sorbitan mono- and diesters of fatty acids preferably containing from 12 to 22 carbon atoms, are also suitable. The ratio by weight of hydrophilic to lipophilic groups in these ethylene oxide adducts should be such that the weight of the hydrophilic groups, i.e. the weight of the polyethylene glycol ether groups (formed by the ethylene oxide) and the polyol groups (in the case of fatty acid-polyol partial ester adducts), makes up around 60 to 80% by weight of the total molecule of the ethylene oxide adducts. Accordingly, in these ethylene oxide adducts suitable for the preparation of pearlescent concentrates according to the invention, the HLB-value (calculated as $HLB=(E+P)/5$, where E is the ethylene oxide content in % by weight and P is the polyhydric alcohol content in % by weight in the adduct) is in the range of from 12 to 16. The amount of ethoxylation for a given compound should be appropriate to yield an ethoxylated compound within the above HLB range.

Particularly suitable nonionic ethylene oxide adducts are the adducts of from 6 to 20 mols of ethylene oxide with $C_{12-22}$ fatty alcohols.

The pearlescent concentrates according to the invention have a preferable and particularly silky to metallic pearlescence where, as pearlizer ingredient A, there is present a combination of:

(A1) from 5 to 8% by weight of a mixture of ethylene glycol mono- and distearate, preferably in a ratio by weight of from 1:2-5; and (A2) from 2 to 5% by weight of a triethylene glycol distearate.

Particularly high stability of the pearlescent concentrates is obtained where ingredient C is a combination of:

(C1) from 1 to 3% by weight of an adduct of from 8 to 15 mols of ethylene oxide with a $C_{12-18}$ coconut oil fatty alcohol cut and (C2) from 0.5 to 2% by weight of an adduct of from 10 to 20 mols of ethylene oxide with a saturated $C_{16-18}$ fatty alcohol cut.

Suitable $C_{12-18}$ coconut oil fatty alcohol cuts are obtained from coconut oil by catalytic hydrogenation of the unsaturated fractions, transesterification to the saturated coconut oil fatty acid methylester, catalytic hydrogenation to the saturated coconut oil fatty alcohol and separation of the $C_{6-8}$ and $C_{10}$ fatty alcohols (i.e. precut coconut oil fatty alcohols) by distillation. Suitable $C_{16-18}$ fatty alcohol cuts may be similarly obtained from numerous vegetable and animal fats and oils. The addition of ethylene oxide onto fatty alcohol cuts of this type is carried out by methods known from the literature, for example in a pressure vessel at temperatures of from 140° to 200° C. and in the presence of basic catalysts such as potassium hydroxide or sodium hydroxide, and/or calcium acetate.

The pearlescent concentrates according to the invention are free-flowing at ambient temperature, i.e. at temperatures of from 10° to 30° C., in other words they may be poured out from vessels or pumped through pipes without any need for additional heating. Particularly good flow combined with adequate dispersion stability is shown by the pearlescent concentrates according to the invention in cases where components A and B together make up from 8 to 14% by weight of the concentrate.

A pearlescent concentrate according to the invention which may be pumped at temperatures as low as about +5° C., and is therefore a preferred embodiment, comprises (in addition to water):

(A1) approximately 6% by weight of a mixture of ethylene glycol mono- and distearate in a ratio by weight of 1:2-5;

(A2) approximately 4% by weight of triethylene glycol distearate;

(B) from 2 to 4% by weight of a $C_{12-18}$ coconut oil fatty acid monoethanolamide;

(C1) approximately 2% by weight of an adduct of from 8 to 12 mols of ethylene oxide with a saturated $C_{12-18}$ coconut oil fatty alcohol cut; and (C2) approximately 1% by weight of an adduct of from 10 to 16 mols of ethylene oxide with a saturated $C_{16-18}$ fatty alcohol cut.

Instead of using ethylene glycol mono- and distearate and triethylene glycol distearate, it is also possible to use the corresponding esters of palmitic acid-stearic acid mixtures, provided at least 50% by weight of stearic acid is present in the mixture.

In addition to the compulsory components mentioned, the pearlescent concentrates according to the invention essentially contain water. They preferably may also contain small quantities of preservatives, for example formaldehyde, sodium benzoate, sorbic acid, p-hydroxybenzoic acid ester, 5-bromo-5-nitro-1,3-dioxane, or other preservatives suitable for aqueous preparations. Buffers for adjusting the pH to values of from 6 to 8, for example citric acid and/or sodium citrate, may also be present in small quantities.

The pearlescent concentrates according to the invention are preferably produced by initially heating components A, B and C together beyond their combination melting point, preferably to a temperature of from 75° to 100° C., and then mixing them. The water, which is also heated to 75°-100° C., is then added with stirring to the resulting melt. The water may already contain preservatives and buffers. The emulsion formed is then cooled with stirring to approximately 50° C. over a period of 5 to 20 minutes and briefly homogenized, typically for 1 to 3 minutes, at that temperature using a homogenizer or dispersion unit generating powerful shear forces. Static and dynamic mixing units, for example split homogenizers or dispersion units functioning on the stator-rotor principle, may be used for this purpose. After this brief and intensive homogenization, the dispersion formed is further cooled with slow stirring to room temperature.

The pearlescent concentrates according to the invention are suitable for producing pearlescence in aqueous surfactant preparations of any ionicity and in aqueous cosmetic preparations, irrespective of whether these prepartions contain cationic or anionic surfactants or polymers. For producing pearlescence, a pearlescent-effective amount, preferably from 1 to 10% by weight of the pearlescent concentrates according to the invention are dispersed in the aqueous preparation (based upon the weight of the finished preparation). The pearlescent concentrates may be dispersed with gentle stirring at ambient temperatures of from about 10° to 30° C., i.e. without heating.

The following Examples are intended to illustrate the invention without limiting it in any way. Alternate nomenclature, where given, is that of the Cosmetic, Toiletry, and Fragrance Association (CTFA).

EXAMPLES

| 1. Preparation of a free-flowing pearlescent concentrate | |
|---|---|
| Formulation: | |
| Ethylene glycolstearate (CTFA name: glycol distearate) | 6.0 g |
| Triethylene glycol distearate (hydroxyl number 13.5) (CTFA name: PEG-3-distearate) | 4.0 g |
| $C_{12-18}$ coconut oil fatty acid monoethanolamide | 3.5 g |
| $C_{12-18}$ coconut oil fatty alcohol +10 mols E.O. | 2.0 g |
| $C_{16-18}$ fatty alcohol (1:1) +12 mols E.O. | 1.0 g |
| Formaldehyde solution (10%) | 0.15 g |
| Water q.s. to | 100.0 g |
| Citric acid solution (1%) to pH = 6.5-7.5 | |

Procedure:

The fatty components were heated together beyond their melting point and mixed at 85° C. The formaldehyde solution, the water and the citric acid solution were also mixed, heated to 85° C. and added with stirring to the melt of the fatty components. After stirring for 5 to 10 minutes, the dispersion was cooled to 50° C. in 10 minutes with continued stirring and then homogenized for 2 minutes at 50° C. using a "KIA UltraTurrax" T 45 disperser. The dispersion was then cooled to room temperature (approx. 25° C.) with slow stirring.

A white-pearlescent liquid dispersion having the following characteristics was obtained:
Solids content: 16.5% by weight
pH-value (1% solution): 6.9
Viscosity (+20° C.): 3500 mPa.s (Hoeppler falling ball viscosimeter)
Viscosity (+5° C.): 1300 mPa.s (Hoeppler falling ball viscosimeter)

2. Application Examples

2.1 Ampholytic hairwashing preparation

| | |
|---|---|
| N—cocoacylamidopropyl dimethylglycine (30%) (CTFA name: cocoamidopropylbetaine) | 30.0 g |
| Polyol fatty acid ester (CTFA name: PEG-7-glyceryl cocoate) | 2.0 g |
| Coconut oil fatty acid diethanolamide (CTFA name: cocamide DEA) | 4.0 g |
| Pearlescent concentrate of Example 1 | 5.0 g |
| 5-bromo-5-nitro-1,3-dioxane, 10% solution in 1,2-propylene glycol | 0.2 g |
| Sodium chloride | 1.0 g |
| Citric acid solution, 10% in water | 0.5 g |
| Water q.s. to | 100.0 g |

2.2 Anionic shampoo

| | |
|---|---|
| $C_{12-14}$ fatty alcohol polyglycolether sulfate | 38.0 g |
| N—cocosacylamidoethyl-hydroxyethylcarboxymethylglycine (CFTA name: cocoemphocarboxyglycinate) | 10.0 g |
| Polyol fatty acid ester (CTFA name: PEG-7-glycerol cocoate) | 2.0 g |
| Coconut oil fatty acid diethanolamide | 2.0 g |
| Sodium chloride | 1.5 g |
| Pearlescent concentrate of Example 1 | 5.0 g |
| 5-bromo-5-nitro-1,3-dioxane, 10% in solution in 1,2-propylene glycol | 0.2 g |
| Citric acid solution, 10% in water | 0.1 g |
| Water q.s. to | 100.0 g |

2.3 Quick hair treatment

| | |
|---|---|
| Tris-(oligooxyethyl)-alkylammonium phosphate (CTFA name: quaternium -52) | 2.0 g |
| Polyol fatty acid ester (CTFA name: PEG-7-glyceryl cocoate) | 0.5 g |
| Hydroxyethylcellulose 2% in water | 50.0 g |
| Pearlescent concentrate of Example 1 | 2.0 g |
| Citric acid | 0.2 g |
| Water | 45.0 g |

2.4 Quick hair treatment

| | |
|---|---|
| Polyglycol-polyamine condensation resin (CTFA name: PEG-15-tallow polyamine) | 5.0 g |
| Hydroxyethylcellulose, 2% in water | 93.0 g |
| Pearlescent concentrate of Example 1 | 2.0 g |

I claim:

1. A pearlescent concentrate in the form of a free-flowing dispersion essentially free from ionic surfactants, consisting of:
   (A) from about 5 to about 15% at least one ester of the formula $R^1$—$(OC_nH_{2n})_x$—$OR^2$, wherein
   $R^1$ is a linear $C_{16-22}$ fatty acyl,
   $R^2$ is a linear $C_{16-22}$ fatty acyl or hydrogen,
   n is 2 or 3, and
   x is an integer from 1 to 14;
   (B) from about 1 to about 6% of at least one $C_{12-22}$ fatty acid monoethanolamide;
   (C) from about 1 to about 5% of at least one nonionic ethylene oxide adduct of fatty alcohol, fatty acid, fatty amide, or alkanolamide having 12 to 22 carbon atoms in the alkyl or acyl moiety, or a $C_{8-16}$ alkylphenol; having an HLB-value of about 12 to about 16; and
   (D) water q.s. to 100%; all percentages being based upon the total weight of said pearlescent concentrate.

2. The concentrate of claim 1 wherein
   (A) is at least one: monoester or diester of ethylene glycol or propylene glycol with at least one higher fatty acid; or diester of diethylene glycol or triethylene glycol with at least one higher fatty acid.

3. The concentrate of claim 1 wherein
   (A) is at least one monoester or diester of ethylene glycol or propylene glycol with palmitic acid, stearic acid, and/or behenic acid; or diester of diethylene glycol or triethylene glycol with palmitic acid, stearic acid, and/or behenic acid.

4. The concentrate of claim 2 wherein said at least one higher fatty acid is hardened tallow fatty acid.

5. The concentrate of claim 2 wherein said at least one higher fatty acid is a saturated $C_{16-18}$ fatty acid fraction of tallow fatty acid.

6. The concentrate of claim 2 wherein:
   (A) is the ethylene glycol monoester and/or diester of palmitic acid, and/or stearic acid.

7. The concentrate of claim 2 wherein (A) is:
   (A1) from about 5 to about 8% of a mixture of ethylene glycol monostearate and ethylene glycol distearate; and
   (A2) from about 2 to about 5% of triethylene glycol distearate.

8. The concentrate of claim 7 wherein in (A1) the ratio by weight of monostearate:distearate is about 1:2-5.

9. The concentrate of claim 1 wherein:
   (B) is at least one $C_{12-18}$ fatty acid monoethanolamide.

10. The concentrate of claim 1 wherein:
    (B) is lauric acid monoethanolamide, myristic acid monoethanolamide, palmitic acid monoethanolamide, stearic acid monoethanolamide, a mixture of palmitic acid monoethanolamide and stearic acid monoethanolamide, the monoethanolamide of the $C_{12-18}$ fraction of coconut oil fatty acid, or a mixture thereof.

11. The concentrate of claim 2 wherein:
    (B) is lauric acid monoethanolamide, myristic acid monoethanolamide, palmitic acid monoethanolamide, stearic acid monoethanolamide, a mixture of palmitic acid monoethanolamide and stearic acid monoethanolamide, the monoethanolamide of the $C_{12-18}$ fraction of coconut oil fatty acid, or a mixture thereof.

12. The concentrate of claim 3 wherein:
    (B) is lauric acid monoethanolamide, myristic acid monoethanolamide, palmitic acid monoethanolamide, stearic acid monoethanolamide, a mixture of palmitic acid monoethanolamide and stearic acid monoethanolamide, the monoethanolamide of the $C_{12-18}$ fraction of coconut oil fatty acid, or a mixture thereof.

13. The concentrate of claim 7 wherein:
    (B) is lauric acid monoethanolamide, myristic acid monoethanolamide, palmitic acid monoethanolamide, stearic acid monoethanolamide, a mixture of palmitic acid monoethanolamide and stearic acid monoethanolamide, the monoethanolamide of the $C_{12-18}$ fraction of coconut oil fatty acid, or a mixture thereof.

14. The concentrate of claim 1 wherein:
    (C) is at least one ethylene oxide adduct of a fatty alcohol, fatty acid, fatty amide, or alkanolamide, 15. The concentrate of claim 2 wherein:
(C) is at least one ethylene oxide adduct of a fatty alcohol, fatty acid, fatty amide, or alkanolamide, any fatty alkyl moiety or fatty acyl moiety present having 12 to 22 carbon atoms.

16. The concentrate of claim 1 wherein:
(C) is an ethylene oxide adduct with: a ($C_{8-16}$-alkyl) phenol, a glycerol monoester, a pentaerythritol monoester, a sorbitan monoester, or a fatty acid diester, each containing 12 to 22 carbon atoms; or a mixture thereof.

17. The concentrate of claim 3 wherein:
(C) is an ethylene oxide adduct with: a ($C_{8-16}$-alkyl) phenol, a glycerol monoester, a pentaerythritol monoester, a sorbitan monoester, or a fatty acid diester, each containing 12 to 22 carbon atoms; or a mixture thereof.

18. The concentrate of claim 1 wherein:
(C) is an ethylene oxide adduct with: a ($C_{8-16}$-alkyl) phenol, a glycerol monoester, a pentaerythritol monoester, a sorbitan monoester, or a fatty acid diester, each containing 12 to 22 carbon atoms; or a mixture thereof.

19. The concentrate of claim 1 wherein:
(C) is an adduct of 6 to 20 mols of ethylene oxide with at least one $C_{12-22}$ fatty alcohol.

20. The concentrate of claim 13 wherein:
(C) is an adduct of 6 to 20 mols of ethylene oxide with at least one $C_{12-22}$ fatty alcohol.

21. The concentrate of claim 1 wherein (C) is:
(C1) from about 1 to about 3% of an adduct of from 8 to 15 mols of ethylene oxide with $C_{12-18}$ coconut oil fatty alcohol cut; and
(C2) from about 0.5 to about 2% of an adduct of from 10 to 20 mols of ethylene oxide with a saturated $C_{16-18}$ fatty alcohol cut.

22. The concentrate of claim 7 wherein (C) is:
(C1) from about 1 to about 3% of an adduct of from 8 to 15 mols of ethylene oxide with $C_{12-18}$ coconut oil fatty alcohol cut; and
(C2) from about 0.5 to about 2% of an adduct of from 10 to 20 mols of ethylene oxide with a saturated $C_{16-18}$ fatty alcohol cut.

23. The concentrate of claim 13 wherein (C) is:
(C1) from about 1 to about 3% of an adduct of from 8 to 15 mols of ethylene oxide with $C_{12-18}$ coconut oil fatty alcohol cut; and
(C2) from about 0.5 to about 2% of an adduct of from 10 to 20 mols of ethylene oxide with a saturated $C_{16-18}$ fatty alcohol cut.

24. The concentrate of claim 1 wherein:
(D) is present in about 75 to about 90%.

25. The concentrate of claim 1 wherein:
(A) and (B) together are present in about 8 to about 14%.

26. The concentrate of claim 1 wherein:
(A) is
 (A1) about 6% of a mixture of ethylene glycol monostearate and distearate in a weight ratio of 1:2-5, and
 (A2) about 4% of triethylene glycol distearate;
(B) is about 2 to about 4% of a $C_{12-18}$ coconut fatty acid monoethanolamide;
(C) is
 (C1) about 2% of an adduct of 8 to 12 mols of ethylene oxide with a $C_{12-18}$ coconut oil fatty alcohol cut, and
 (C2) about 1% of an adduct of 10 to 16 mols of ethylene oxide with a saturated $C_{16-18}$ fatty alcohol cut.

27. A method for imparting a pearlescent appearance to an aqueous surfactant composition or aqueous cosmetic composition comprising dispersing therein an amount of the concentrate of claim 11 effective to provide a pearlescent appearance.

28. The method of claim 27 wherein about 1 to about 10% by weight of said concentrate are added, based upon the total weight of said surfactant composition or cosmetic composition.

29. A pearlescent concentrate in the form of a free-flowing dispersion essentially free from ionic surfactants, consisting of:
(A) from about 5 to about 15% of at least one ester of the formula $$R^1-(OC_nH_{2n})_x-OR^2,$$

wherein
$R^1$ is a linear $C_{16-22}$ fatty acyl,
$R^2$ is a linear $C_{16-22}$ fatty acyl or hydrogen,
n is 2 or 3, and
x is an integer from 1 to 4;
(B) from about 1 to about 6% of at least one $C_{12-22}$ fatty acid monoethanolamide;
(C) from about 1 to about 5% of at least one nonionic ethylene oxide adduct having an HLB-value of about 12 to about 16; and
(D) water q.s. to 100%; all percentages being based upon the total weight of said pearlescent concentrate.

* * * * *